(12) United States Patent
Bonnert et al.

(10) Patent No.: US 6,958,344 B2
(45) Date of Patent: Oct. 25, 2005

(54) PYRIMIDINE COMPOUNDS AND THEIR USE AS MODULATORS OF CHEMOKINE RECEPTOR ACTIVITY

(75) Inventors: Roger Bonnert, Loughborough (GB); Peter Cage, Loughborough (GB); Fraser Hunt, Loughborough (GB); Iain Walters, Loughborough (GB); Paul Willis, Loughborough (GB)

(73) Assignee: AstraZeneca AB (SE)

( * ) Notice: Subject to any disclaimer, the term of this patent is extended or adjusted under 35 U.S.C. 154(b) by 172 days.

(21) Appl. No.: 10/203,584

(22) PCT Filed: Feb. 7, 2001

(86) PCT No.: PCT/SE01/00245

§ 371 (c)(1),
(2), (4) Date: Aug. 9, 2002

(87) PCT Pub. No.: WO01/58902

PCT Pub. Date: Aug. 16, 2001

(65) Prior Publication Data

US 2003/0040523 A1 Feb. 27, 2003

(30) Foreign Application Priority Data

Feb. 11, 2000 (GB) .............................................. 0003019

(51) Int. Cl.⁷ .................... C07D 473/24; C07D 487/04; A61K 31/52; A61K 31/519; A61P 29/00
(52) U.S. Cl. ............................ 514/263.37; 514/263.38; 544/276; 544/280
(58) Field of Search ..................... 544/276; 514/263.37, 514/263.38

(56) References Cited

U.S. PATENT DOCUMENTS

| | | | |
|---|---|---|---|
| 3,318,900 A | 5/1967 | Janssen | |
| 4,126,689 A | 11/1978 | Sanczuk et al. | |
| 4,278,677 A | 7/1981 | Nedelec et al. | |
| 4,410,528 A | 10/1983 | Teranishi et al. | |
| 5,521,197 A | 5/1996 | Audia | |
| 6,172,067 B1 | 1/2001 | Ito et al. | |
| 6,248,755 B1 | 6/2001 | Chapman et al. | |
| 6,329,381 B1 * | 12/2001 | Kurimoto et al. ........... | 544/276 |
| 6,407,121 B1 | 6/2002 | Nagamine et al. | |
| 6,432,981 B1 | 8/2002 | Finke et al. | |
| 2003/0032642 A1 * | 2/2003 | Bonnert et al. .......... | 514/234.5 |
| 2003/0119869 A1 * | 6/2003 | Burrows et al. ............ | 514/303 |
| 2004/0157853 A1 * | 8/2004 | Bonnert ....................... | 514/251 |

FOREIGN PATENT DOCUMENTS

| | | | |
|---|---|---|---|
| DE | 2331 223 A1 | 1/1974 | |
| DE | 4119767 A1 | 12/1992 | |
| EP | 0 293 078 A1 | 11/1988 | |
| EP | 0 447 324 A1 | 9/1991 | |
| EP | 0 778 277 A1 | 6/1997 | |
| EP | 1 069 124 A1 | 1/2001 | |
| EP | 1 122 257 A1 | 8/2001 | |
| GB | 2359079 A * | 8/2001 | ......... C07D/473/24 |
| JP | 51-88994 * | 8/1976 | |
| WO | WO 97/40035 | 10/1997 | |
| WO | WO 98/08847 | 3/1998 | |
| WO | WO 98/25617 | 6/1998 | |
| WO | WO 99/04794 | 2/1999 | |
| WO | WO 99/17773 A1 | 4/1999 | |
| WO | WO 99/36421 | 7/1999 | |
| WO | WO 99/51608 | 10/1999 | |
| WO | WO 00/08013 | 2/2000 | |
| WO | WO 00/09511 | 2/2000 | |
| WO | WO 00/38680 A1 | 7/2000 | |
| WO | WO 00/39129 | 7/2000 | |
| WO | WO 00/45800 | 8/2000 | |
| WO | WO 00/59502 A1 | 10/2000 | |
| WO | WO 00/76514 A1 | 12/2000 | |
| WO | WO 01/19825 A1 | 3/2001 | |
| WO | WO 01/25200 A1 | 4/2001 | |
| WO | WO 01/25242 A1 | 4/2001 | |
| WO | WO 01/58907 | 8/2001 | |
| WO | WO 01/62758 | 8/2001 | |
| WO | WO 200158906 A1 * | 8/2001 | ......... A61K/31/519 |
| WO | WO 200166525 A1 * | 9/2001 | ....... A61K/31/4184 |
| WO | WO 200283693 A1 * | 10/2002 | ......... A61K/31/519 |
| WO | 03024966 A1 | 3/2003 | |
| WO | WO 03024966 A1 * | 3/2003 | |

OTHER PUBLICATIONS

Chemical Abstracts, vol. 54, No. 10, May 1960, Abstract No. 9933f, C. Wayne Noell and Roland K. Robins, "Potential Purine Antagonists XVII. Synthesis of 2–methyl and 2–methylthio–6, 8–disubstituted purines", see formula III when R–SMe, R1=Cl, R2=OH.

*Primary Examiner*—Mark L. Berch
(74) *Attorney, Agent, or Firm*—Fish & Richardson, P.C.

(57) ABSTRACT

The invention provides certain heterocyclic compounds, processes, and intermediates used in their preparation, pharmaceutical compositions containing them and their use in therapy; in formula (I), A is a group of formula (a) or (b).

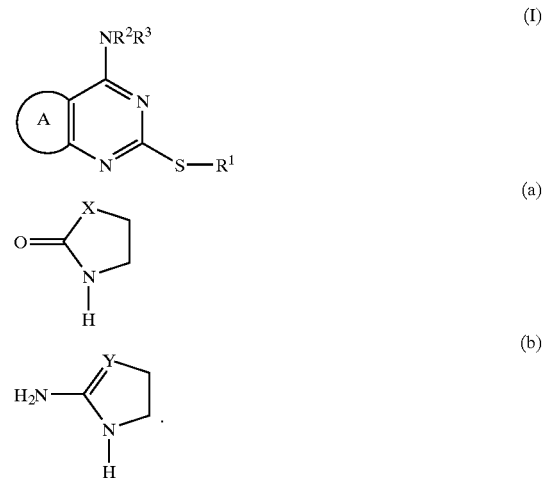

8 Claims, No Drawings

OTHER PUBLICATIONS

U.S. Appl. No. 10/486,503, Bonnert et al. filed Feb. 11, 2004.

Ahmed et al., "Novel synthesis of 1–aryl–9–alkyl–2,3,3a,4, 9,9a–hexahydro–1H–pyrrolo[2,3–b]quinoxalines by lithium aluminum hydride reduction of N–phenyl–1–benzimidazolylsuccinimides", CAPLUS 79:92106 (1973).

Cohen et al., "Cytokine function: A study in biologic diversity", CAPLUS 125:31527 (1996).

Cowley et al., "Preparation of 1–(3–phenyloxpropyl)piperdine derivatives as opioid receptor ligands", CAPLUS 138:39189 (2002).

Finke et al., "Preparation of piperidinylmethylcyclopentanes as modulators of CCR–5 and/or CCR–3 chemokine receptors", CAPLUS 134:56576 (2000) CAS Listing, 77 answers.

Fukuda et al., "Preparation of benzotriazole derivatives as cardiovascular agents and antipsychotics", CAPLUS 123:340149 (1995).

Gewald et al., "New Synthesis of Substituted 4–Amino–quinazolines and Their Heteroanaloga", *J. prakt. Chem.* 338:206–213 (1996).

Grant, "University of Minnesota—Twin Cities Campus College of Pharmacy, Annual Report", [online] 1999, [retrieve on Feb. 13, 2003]. Retrieved from the internet, http://www.msi.umn.edu/general/Reports/ar99/departments/pharmacy.html.

Kiriasis et al., "Synthesis and Properties of New Pteridine Nucleosides", *Dev. Biochem.* 4:49–53 (1978).

McNaught et al., "IUPAC Compendium of Chemical Terminology, 2$^{nd}$ Ed" (1997), Entry for "leaving group".

Ott et al., "4–amino–7, 8–dihydro–2– (methylmercapto)–8–β, –D–ribofuranosylpteridin–7–One, Modified Fusion Reaction with Trimethylsilylated Pteridine Derivatives", *Nucl. Acid. Chem.* 2:735–739 (1978).

Ott et al., "Zur Synthese des 4–Amino–7–oxo–7, 8–dihydropteridin–N–8–β–D–ribofuranosids—ein strukturanaloges Nucleosid des Adenosins", *Chem.Ber.* 107:339–361 (1974).

Patent Abstracts of Japan, abstract of JP–5–202047 A (Chugai Pharmaceut. Co. Ltd.) Aug. 10, 1993.

Sato et al., "Psychotropic agents. 3. 4–(4–Substituted piperidinyl)–1–(4–flurophenyl)–1–butanones with potent neuroleptic activity", CAPLUS 89:208915 (1978).

Sato et al., "Psychotropic Agents, 3. 4–(4–Substituted piperidinyl)–1–(4–flurophenyl)–1–butanones with Potent Neuroleptic Activity," *Journal of Medicinal Chemistry* 21(11):1116–1120 (1978).

Taylor et al., "Molecular Determinants for Recognition of RU 24969 Analogs at Central 5–Hydroxytryptamine Recognition Sites: Use of a Bilinear Function and Substituent Volumes to Describe Steric Fit," *Molecular Pharmacology* 32:42–53 (1988).

Teranishi et al., "Piperidine derivatives and pharmaceutical compositions containing them", CAPLUS 95:132947 (1981).

Trivedi et al., *Annual Reports in Medicinal Chemistry* 35:191–200 (2000).

Vandenberk et al., "1–(Benzazolylalkyl)piperidines and their salts with acids", CAPLUS 87:23274 (1977).

Vartanyan et al., "Synthesis and biological activity of 1–substituted benzimidazole and benztriazole derivatives", CAPLUS 98:4503 (1983).

West, "Solid State Chemistry and its applications", pp. 358, 365 (1988).

* cited by examiner

PYRIMIDINE COMPOUNDS AND THEIR USE AS MODULATORS OF CHEMOKINE RECEPTOR ACTIVITY

CROSS REFERENCE TO RELATED APPLICATIONS

The present application is a national phase application under 35 U.S.C. Section 371 filed from International Patent Application PCT/SE01/00245, filed 7 Feb. 2001, which claims priority to United Kingdom patent application Serial. No. 0003022.1, filed 11 Feb. 2000 and United Kingdom patent application Serial. No. 0003023.9, filed 11 February 2000.

The present invention relates to certain heterocyclic compounds, processes and intermediates used in their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted to molecules are a growing superfamily of 8–14 kDa proteins characterised by a conserved four cysteine motif. At the present time, the chemokine superfamily comprises three groups exhibiting characteristic structural motifs, the C—X—C, C—C and C—X$_3$—C families. The C—X—C and C—C families have sequence similarity and are distinguished from one another on the basis of a single amino acid insertion between the NH-proximal pair of cysteine residues. The C—X$_3$—C family is distinguished from the other two families on the basis of having a triple amino acid insertion between the NH-proximal pair of cysteine residues.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils. Examples include human monocyte chemotactic proteins 1–3 (MCP-1, MCP-2 and MCP3), RANTES (Regulated on Activation, Normal T Expressed and Secreted), eotaxin and the macrophage inflammatory proteins 1α and 1β (MIP-1α and MIP-1β).

The C—X$_3$—C chemokine (also known as fractalkine) is a potent chemoattractant and activator of microglia in the central nervous system (CNS) as well as of monocytes, T cells, NK cells and mast cells.

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX$_3$CR1 for the C—X$_3$—C family. These receptors represent good targets for drug development since agents which modulate these receptors would be useful in the treatment of disorders and diseases such as those mentioned above.

The present invention therefore provides compounds of formula (I) and pharmaceutically acceptable salts or solvates thereof:

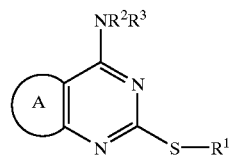

(I)

in which:
A is a group of formula (a) or (b):

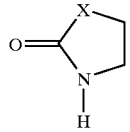

(a)

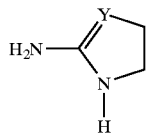

(b)

R$^1$ represents a C$_3$–C$_7$ carbocyclic, C$_1$–C$_8$ alkyl, C$_2$–C$_6$ alkenyl or C$_2$–C$_6$ alkynyl group, the latter four groups may be optionally substituted by one or more substituent groups independently selected from halogen atoms, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^{10}$, of which can be optionally substituted by one or more substituents independently selected from halogen atoms, cyano, nitro, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^{10}$ groups;

R$^2$ and R$^3$ each independently represent hydrogen, a C$_3$–C$_7$ carbocyclic group, C$_1$–C$_8$ alkyl, C$_2$–C$_6$ alkenyl or C$_2$–C$_6$ alkynyl group, the latter four groups may be optionally substituted by one or more substituent groups independently selected from halogen atoms, —OR$^4$, —NR$^5$R$^6$ —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^{10}$ or R$^2$ and R$^3$ together form a 3–8 membered ring optionally containing one or more atoms selected from O, S, NR$^8$ and itself optionally substituted by C$_{1-3}$-alkyl, halogen, R$^4$ represents hydrogen, C$_1$–C$_6$ alkyl or a phenyl group the latter two of which may be optionally substituted by one or more substituent groups independently selected from halogen atoms, phenyl, —OR$^{11}$ and —NR$^{12}$R$^{13}$;

R$^5$ and R$^6$ independently represent a hydrogen atom or a C$_1$–C$_6$ alkyl or phenyl group the latter two of which may be optionally substituted by one or more substituent groups independently selected from halogen atoms, phenyl, —OR$^{14}$ and —NR$^{15}$R$^{16}$, —CONR$^{15}$R$^{16}$, —NR$^{15}$COR$^{16}$, —SO$_2$NR$^{15}$R$^{16}$, NR$^{15}$SO$_2$R$^{16}$ or R$^5$ and R$^6$ together with the nitrogen atom to which they are attached form a 4- to 7-membered saturated heterocyclic ring system optionally comprising a further heteroatom selected from oxygen and nitrogen atoms, which ring system may be optionally substituted by one or more substituent groups independently selected from phenyl, —OR$^{14}$, —COOR$^{14}$, —NR$^{15}$R$^{16}$, —CONR$^{15}$R$^{16}$, —NR$^{15}$COR$^{16}$, —SO$_2$NR$^{15}$R$^{16}$, NR$^{15}$SO$_2$R$^{16}$ or C$_1$–C$_6$ alkyl, itself optionally substituted by one or more substituents independently selected from halogen atoms and —NR$^{15}$R$^{16}$ and —OR$^{17}$ groups;

R$^{10}$ represents a C$_1$–C$_6$ alkyl group or phenyl group, each of which may be optionally substituted by one or more substituent groups independently selected from halogen atoms, phenyl, —OR$^{17}$ and —NR$^{15}$R$^{16}$;

X is NH or CR$^{18}$R$^{19}$;

Y is N or CR$^{18}$; and each of R$^7$, R$^8$, R$^9$, R$^{11}$, R$^{12}$, R$^{13}$, R$^{14}$ R$^{15}$, R$^{16}$, R$^{17}$, R$^{18}$, R$^{19}$ independently represent a hydrogen atom, C$_1$–C$_6$, alkyl, or a phenyl group.

In the context of the present specification, unless otherwise indicated, an alkyl or alkenyl group or an alkyl or alkenyl moiety in a substituent group may be linear or branched.

Aryl groups include phenyl and naphthyl. Heteroaryl is defined as a 5- or 6-membered aromatic ring optionally containing one or more heteroatoms selected from N, S, O. Examples include pyridine, pyrimidine, thiazole, oxazole, pyrazole, imidazole, furan. Heterocyclic rings as defined for R$^5$ and R$^6$ means saturated heterocycles, examples of which include morpholine, azetidine, pyrrolidine, piperidine and piperazine.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

In formula (I) above, A represents a sub-group of formula (a) or (b). Preferably A is a group of formula (b) and Y is N.

Suitably the group R$^1$ represents a C$_3$–C$_7$ carbocyclic, C$_1$–C$_8$ alkyl, C$_2$–C$_6$ alkenyl or C$_2$–C$_6$ alkynyl group, the latter four groups may be optionally substituted by one or more substituent groups independently selected from halogen atoms, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^{10}$, an aryl or heteroaryl group each of which can be optionally substituted by one or more substituents independently selected from halogen atoms, cyano, nitro, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^{10}$, C$_1$–C$_6$ alkyl or trifluoromethyl groups. Particularly advantageous compounds of formula (I) are those in which R represents an optionally substituted benzyl group. More preferably R$^1$ represents benzyl or benzyl substituted by one or more halogen atoms, in particular benzyl substituted by two fluorine atoms.

Suitably R$^2$ and R$^3$ each independently represent hydrogen, a C$_3$–C$_7$ carbocyclic group, C$_1$–C$_8$ alkyl, C$_2$–C$_6$ alkenyl or C$_2$–C$_6$ alkynyl group, the latter four groups may be optionally substituted by one or more substituent groups independently selected from halogen atoms, —OR$^4$, —NR$^5$R$^6$ —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^{10}$, or R$^2$ and R$^3$ together form a 3–8 membered ring optionally containing one or more atoms selected from O, S, NR$^8$ and itself optionally substituted by C$_{1-3}$-alkyl, halogen.

Preferably one of R$^2$ and R$^3$ is hydrogen and the other is C$_3$–C$_8$ alkyl substituted by one or more hydroxy groups. More preferably one of R$^2$ and R$^3$ is hydrogen and the other is CH(CH$_3$)CH$_2$OH, CH(Et)CH$_2$OH, C(CH$_3$)$_2$CH$_2$OH or CH(CH$_2$OH)$_2$. When one of R$^2$ and R$^3$ is hydrogen and the other is CH(CH$_3$)CH$_2$OH or CH(Et)CH$_2$OH the resulting compounds of formula (I) are preferably in the form of the (R) isomer. Most preferably one of R$^2$ and R$^3$ is hydrogen and the other is CH(CH$_3$)CH$_2$OH.

Particularly preferred compounds of the invention include:

2-[[(2,3-Difluorophenyl)methyl]thio]-5,7-dihydro-4-[[(1R)-2-hydroxy-1-methylethyl]amino]-6H-pyrrolo[2,3-d]pyrimidin-6-one, 7,9-dihydro-6-[[(1R)-2-hydroxy-1-methylethyl]amino]-2-[(phenylmethyl)thio]-8H-purin-8-one, 4-amino-2-[[(2,3-difluorophenyl)methyl]thio]-5,7-dihydro-6H-pyrrolo[2,3d]pyrimidin-6-one, (2R)-2-[[8-amino-2-[[(2-fluorophenyl)methyl]thio]-9H-purin-6-yl]amino]-1-propanol, 2-[[8-amino-2-[[(2,3-difluorophenyl)methyl]thio]-9H-purin-6-yl]amino]-1,3-propanediol, 2-[[8-amino-2-[[(2,3-difluorophenyl)methyl]thio]-9H-purin-6-yl]amino]-2-methyl-1-propanol, (2R)-2-[[8-amino-2-[[(2,3-difluorophenyl)methyl]thio]-9H-purin-6-yl]amino]-1-butanol, 2-[[8-amino-2-[[(2,3-difuorophenyl)methyl]thio]-9H-purin-6-yl]amino]-2-methyl-1,3-propanediol, (2R)-2-[[8-amino-2-[[(2,3-difluorophenyl)methyl]thio]-9H-purin-6-yl]amino]-1-propanol, 2-[[8-amino-2-[[(2,3-difluorophenyl)methyl]thio]-9H-purin-6-yl]amino]-ethanol, (2R)-2-[[8-amino-2-[[(3-chlorophenyl)methyl]thio]-9H-purin-6-yl]amino]-1-propanol, (2R)-2-[[8-amino-2-[(phenylmethyl)thio]-9H-purin-6-yl]amino]-1-propanol, (2R)-2-[[8-amino-2-[[(3-methylphenyl)methyl]thio]-9H-purin-6-yl]amino]-1-propanol, (2R)-2-[[8-amino-2-[[(2-methylphenyl)methyl]thio]-9H-purin-6-yl]amino]-1-propanol, (2R)-2-[[8-amino-2-[[(3-methoxyphenyl)methyl]thio]-9H-purin-6-yl]amino]-1-propanol, (2R)-2-[[8-amino-2-[[(4-methylphenyl)methyl]thio]-9H-purin-6-yl]amino]-1-propanol, (2R)-2-[[8-amino-2-[[(2-bromophenyl)methyl]thio]-9H-purin-6-yl]amino]-1-propanol, (2R)-2-[[8-amino-2-[[(3-chloro-2-fluorophenyl)methyl]thio]-9H-purin-6-yl]amino]-1propanol, (2R)-2-[[8-amino-2-[[(3-chloro-4-methoxyphenyl)methyl]thio]-9H-purin-6-yl]amino]-1-propanol, (2R)-2-[[8-amino-2-[(1,3-benzodioxol-4-ylmethyl)thio]-9H-purin-6-yl]amino]-1-propanol and pharmaceutically acceptable salts and solvates thereof According to the invention there is also provided a process for the preparation of: (a) a compound of formula (I) where A is a sub-group of formula (a) and X is CH$_2$ which comprises treatment of a compound of formula (II):

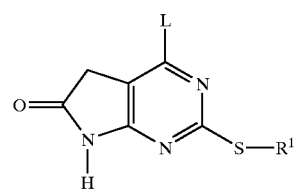

(II)

where R$^1$ is as defined in formula (I) and L is a leaving group such as chlorine with an amine HNR$^2$R$^3$ and optionally forming a pharmaceutically acceptable salt. The reaction can be carried out in a solvent such as N-methylpyrrolidinone at elevated temperature, for example at between 0° C. and 150° C.

Compounds of formula (II) where R$^1$ is as defined in formula (I) and L is a halogen may be prepared by heating a compound of formula (III) where R$^1$ is as defined above and L is a halogen in the presence of an acid catalyst such as p-toluene sulphonic acid. The reaction can be carried out in a solvent such as toluene at elevated temperature, for example at reflux.

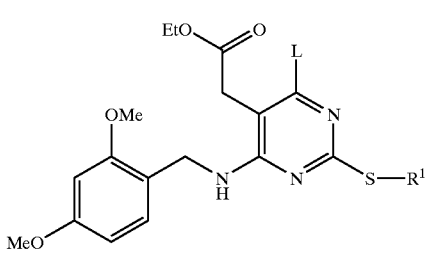

(III)

Compounds of formula (III) where $R^1$ is as defined in formula (I) and L is a halogen may be prepared by treating a compound of formula (IV) where $R^1$ is as defined above and L is a halogen with 2,4-dimethoxybenzylamine in the presence of a base such as N,N'-diisopropylethylamine. The reaction may be carried out in a solvent such as dimethylformamide between 0° C. and 100° C.

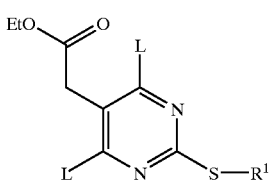

(IV)

Compounds of formula (IV) where $R^1$ is as defined in formula (I) and L is a halogen may be prepared by treating a compound of formula (IV) where $R^1$ is as defined in formula (I) and L is an hydroxyl group with a halogenating agent such as phosphorus oxychloride. The reaction may be carried out at reflux in the presence of dimethylaniline.

Compounds of formula (IV) where $R^1$ is as defined in formula (I) and L is an hydroxyl group are suitably prepared by reacting a compound of formula (V):

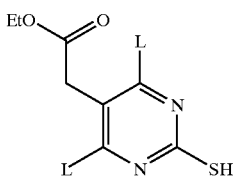

(V)

with a compound of formula $R^1X$ where $R^1$ is as defined above and X is a leaving group such as bromide in the presence of a base such as sodium hydride. The reaction may be carried out in a solvent such as dimethylformamide at room temperature.

The compound of formula (V) where L is a hydroxyl group may be suitably prepared by treating 1,1,2-ethane tricarboxylate with thiourea in the presence of a base such as sodium ethoxide. The reaction may be carried out in a solvent such as ethanol at reflux.

(b) a compound of formula (I) where A is a sub-group of formula (a) and X is NH which comprises treatment of a compound of formula (VI):

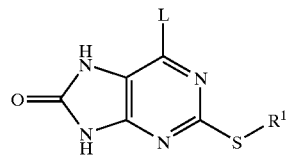

(VI)

where $R^1$ is as defined in formula (I) and L is a leaving group such as chlorine with an amine $HNR^2R^3$ and optionally forming a pharmaceutically acceptable salt. The reaction can be carried out in a solvent such as N-methylpyrrolidinone at elevated temperature, for example at between 0° C. and 150° C.

Compounds of formula (VI) where $R^1$ is as defined in formula (I) and L is a leaving group such as chlorine may be prepared from compounds of formula (VII) where $R^1$ and L are as defined above by treatment with phosgene or an equivalent reagent such as triphosgene. The reaction may be carried out in a solvent such as dichloromethane in the presence of a base such as triethylamine at room temperature or below.

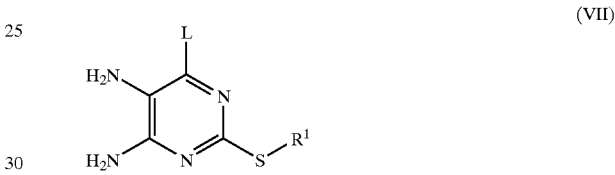

(VII)

Compounds of formula (VII) where $R^1$ is as defined in formula (I) and L is a leaving group such as chlorine may be prepared from compounds of formula (VIII) where $R^1$ and L are as defined above by treatment with a reducing agent such as iron. The reaction may be carried out in a solvent such as aqueous ethanol in the presence of ammonium chloride at a temperature between 0° C. and 100° C.

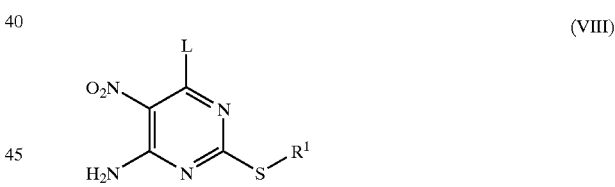

(VIII)

Compounds of formula (VIII) where $R^1$ is as defined in formula (I) and L is a leaving group such as chlorine may be prepared from compounds of formula (IX) where $R^1$ and L are as defined above by treatment with ammonia. The reaction may be carried out in a solvent such as tetrahydrofuran in the presence of a base such as diisopropylamine at a temperature between 0° C. and 100° C.

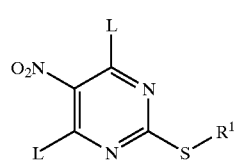

(IX)

Compounds of formula (IX) where $R^1$ is as defined in formula (I) and L is a leaving group such as chlorine may be prepared from compounds of formula (IX) where $R^1$ is as defined in formula (I) and L is hydroxy by treatment with a halogenating agent such as phosphorus oxychloride. The reaction may be carried out in the presence of a base such as 1-methylimidazole at a temperature between 0° C. and 150° C.

Compounds of formula (IX) where $R^1$ is as defined in formula (I) and L is hydroxy may be prepared from compounds of formula (X) where $R^1$ is as defined in formula (I) and L is hydroxy by treatment with a nitrating agent such as concentrated nitric acid. The reaction may be performed in a solvent such as glacial acetic acid at a temperature between 0° C. and 150° C.

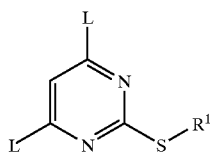

(X)

Compounds of formula (X) where $R^1$ is as defined in formula (I) and L is hydroxy may be prepared from compounds of formula (XI) by treatment with a compound of formula $R^1X$ where $R^1$ is as defined above and X is a leaving group such as bromide. The reaction may be carried out in a solvent such as aqueous NMP using a base such as sodium hydroxide at room temperature.

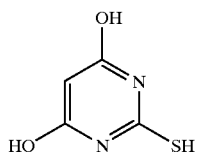

(XI)

(c) a compound of formula (I) where A is a sub-group of formula (b) and Y is N which comprises either:

i) treatment of a compound of formula (XII):

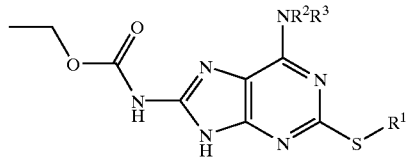

(XII)

where $R^1$, $R^2$ and $R^3$ are as defined in formula (I) with a hydrolysing agent such as lithium hydroxide. The reaction may be performed in a solvent such as aqueous dioxan at a temperature between 0° C. and 100° C.

Compounds of formula (XII) where $R^1$, $R^2$ and $R^3$ are as defined in formula (I) may be prepared by treatment of compounds of formula (XIII) with ethoxycarbonylisothiocyanate followed by a dehydrating agent such as diisopropylcarbodiimide. The reaction may be carried out in a solvent such as acetonitrile at a temperature between 0° C. and 100° C.

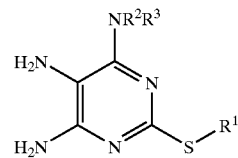

(XIII)

Compounds of formula (XIII) where $R^1$, $R^2$ and $R^3$ are as defined in formula (I) may be prepared by treatment of compounds of formula (XIV) where $R^1$, $R^2$ and $R^3$ are as defined above with a reducing agent such as sodium dithionite. The reaction may be performed in a solvent such as aqueous DMF at a temperature between 0° C. and 150° C.

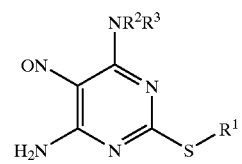

(XIV)

Compounds of formula (XIV) where $R^1$, $R^2$ and $R^3$ are as defined in formula (I) may be prepared by treatment of compounds of formula (XV) where $R^1$, $R^2$ and $R^3$ are as defined above with a nitrosating agent such as sodium nitrite in acetic acid. The reaction may be conveniently carried out at room temperature.

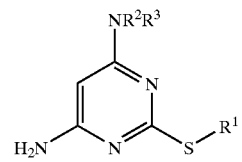

(XV)

Compounds of formula (XV) where $R^1$, $R^2$ and $R^3$ are as defined in formula (I) may be prepared by treatment of compounds of formula (XVI) where $R^1$ is as defined in formula (I) and L is a leaving group such as chloro with an amine $HNR^2R^3$. The reaction can be carried out in a solvent such as N-methylpyrrolidinone at elevated temperature, for example at between 50° C. and 200° C.

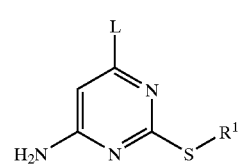

(XVI)

Compounds of formula (XVI) where $R^1$ is as defined in formula (I) and L is a leaving group such as chloro may be prepared by treatment of compounds of formula (XVI) where $R^1$ is as defined in formula (I) and L is hydroxy by treatment with a halogenating agent such as phosphorus oxychloride. The reaction may be carried out in the presence of a base such as 2-picoline at a temperature between 0° C. and 150° C.

Compounds of formula (XVI) where $R^1$ is as defined in formula (I) and L is hydroxy may be prepared from compounds of formula (XVII) by treatment with a compound of formula $R^1X$ where $R^1$ is as defined above and X is a leaving group such as bromide. The reaction may be carried out in a solvent such as aqueous DMF using a base such as potassium hydroxide at room temperature.

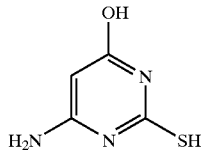

(XVII)

ii) treatment of a compound of formula (XVIII):

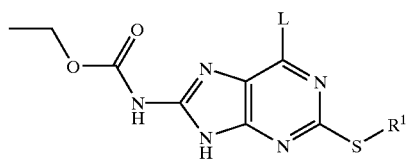

(XVIII)

where R$^1$ is as defined in formula (I) and L is a leaving group such as bromine with an amine HNR$^2$R$^3$. The reaction may be carried out in a solvent such as N-methylpyrrolidinone at elevated temperature, for example at between 50° C. and 200° C.

Compounds of formula (XVIII) where R$^1$ is as defined in formula (I) and L is a leaving group such as bromine may be prepared from compounds of formula (XVIII) where R$^1$ is as defined above and L is NH$_2$ by treatment with a diazotizing agent such as isoamyl nitrite in the presence of a halogenating agent such as bromoform. The reaction may be performed at a temperature between 0° C. and 100° C.

Compounds of formula (XVIII) where R$^1$ is as defined in formula (I) and L is NH$_2$ may be prepared from compounds of formula (XIX) where R$^1$ is as defined above by treatment with ethoxycarbonylisothiocyanate followed by a dehydrating agent such as diisopropylcarbodiimide. The reaction may be carried out in a solvent such as acetonitrile at a temperature between 0° C. and 100° C.

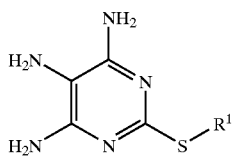

(XIX)

Compounds of formula (XIX) where R$^1$ is as defined in formula (I) may be prepared from compounds of formula (XX) where R$^1$ is as defined above by treatment with a reducing agent such as sodium hydrosulphite. The reaction may be carried out in a solvent such as water at reflux.

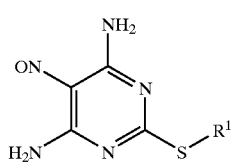

(XX)

Compounds of formula (XX) where R$^1$ is as defined in formula (I) may be prepared by treatment of compounds of formula (XXI) where R$^1$ is as defined above with a nitrosating agent such as sodium nitrite. The reaction may be performed in a solvent such as aqueous acetic acid at a temperature between 0° C. and 100° C.

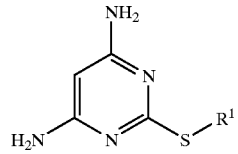

(XXI)

Compounds of formula (XXI) where R$^1$ is as defined in formula (I) may be prepared from compounds of formula (XXII) by treatment with a compound of formula R$^1$X where R$^1$ is as defined above and X is a leaving group such as bromide. The reaction may be carried out in a solvent such as aqueous DMF using a base such as potassium hydroxide at room temperature.

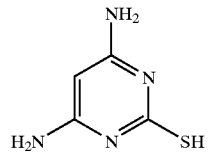

(XXII)

iii) treatment of a compound of formula (XXIII):

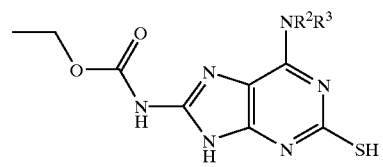

(XXIII)

where R$^2$ and R$^3$ are as defined in formula (I) with a compound of formula R$^1$X where R$^1$ is as defined in formula (I) followed by treatment with a hydrolysing agent such as lithium hydroxide. The alkylation reaction may be performed in a solvent such as DMSO at a temperature between 0° C. and 100° C., and the hydrolysis in a solvent such as aqueous dioxan at reflux.

Compounds of formula (XXIII) where R$^2$ and R$^3$ are as defined in formula (I) may be prepared by treatment of a compound of formula (XII) where R$^1$, R$^2$ and R$^3$ are as defined in formula (I) with sodium in liquid ammonia.

iv) treatment of a compound of formula (XXIV):

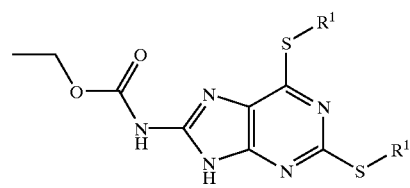

(XXIV)

where R$^1$ is as defined in formula (I) with an amine HNR$^2$R$^3$. The reaction can be carried out in the absence of solvent at elevated temperature, for example between 100° C. and 200° C.

Compounds of formula (XXIV) where R$^1$ is as defined in formula (I) may be prepared by treatment of a compound of formula (XXV) where R$^1$ is as defined above with ethoxycarbonylisothiocyanate followed by a dehydrating agent such as diisopropylcarbodiimide. The reaction may be carried out in a solvent such as acetonitrile at a temperature between 0° C. and 100° C.

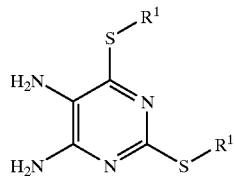

(XXV)

Compounds of formula (XXV) where $R^1$ is as defined in formula (I) may be prepared from compounds of formula (XXVI) by treatment with a compound of formula $R^1X$ where $R^1$ is as defined above and X is a leaving group such as bromide. The reaction may be carried out in a solvent such as methanol using a base such as potassium hydroxide at room temperature.

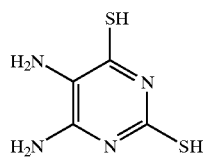

(XXVI)

Compounds of formula (XI), (XVII), (XXII) and (XXVI) are commercially available.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

Novel intermediate compounds form a further aspect of the invention.

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine.

The compounds of formula (I) have activity as pharmaceuticals, in particular as modulators of chemokine receptor (especially CXCR2) activity, and may be used in the treatment (therapeutic or prophylactic) of conditions/diseases in human and non-human animals which are exacerbated or caused by excessive or unregulated production of chemokines. Examples of such conditions/diseases include:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (central and peripheral nervous system) Neurodegenerative diseases and dementia disorders, e.g. Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia; polyneuropathies, e.g. Guillain-Barré syndrome, chronic inflammatory demyelinating polyradiculoneuropathy, multifocal motor neuropathy, plexopathies; CNS demyelination, e.g. multiple sclerosis, acute disseminated/haemorrhagic encephalomyelitis, and subacute sclerosing panencephalitis; neuromuscular disorders, e.g. myasthenia gravis and Lambert-Eaton syndrome; spinal diorders, e.g. tropical spastic paraparesis, and stiff-man syndrome: paraneoplastic syndromes, e.g. cerebellar degeneration and encephalomyelitis; CNS trauma; migraine; and stroke.

(6) (other tissues and systemic disease) atherosclerosis, Acquired Immunodeficiency Syndrome (AIDS), lupus erythematosus, systemic lupus, erythematosus, Hashimoto's thyroiditis, type I diabetes, nephrotic syndrome, eosinophilia fascitis, hyper IgE syndrome, lepromatous leprosy, and idiopathic thrombocytopenia pupura; post-operative adhesions, and sepsis.

(7) (allograft rejection) acute and chronic following, for example, transplantation of kidney, heart, liver, lung, bone marrow, skin and comea; and chronic graft versus host disease;

(8) Cancers, especially non-small cell lung cancer (NSCLC), malignant melanoma, prostate cancer and squamous sarcoma, and tumour metastasis;

(9) Diseases in which angiogenesis is associated with raised CXCR2 chemokine levels (e.g. NSCLC, diabetic retinopathy).

(10) Cystic fibrosis, re-perfusion injury in the heart, brain, peripheral limbs and other organs.

(11) Bum wounds & chronic skin ulcers

(12) Reproductive Diseases (e.g. Disorders of ovulation, menstruation and implantation, Pre-term labour, Endometriosis)

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CXC chemokine receptor subfamily, more preferably the target chemokine receptor is the CXCR2 receptor, Particular conditions which can be treated with the compounds of the invention are psoriasis, diseases in which angiogenesis is associated with raised CXCR2 chemokine levels, and COPD. It is preferred that the compounds of the invention are used to treat psoriasis.

As a further aspect of the present invention, certain compounds of formula (I) may have utility as antagonists of the CX3CR1 receptor. Such compounds are expected to be particularly useful in the treatment of disorders within the central and peripheral nervous system and other conditions characterized by an activation of microglia and/or infiltration of leukocytes (e.g. stroke/ischemia and head trauma).

In a further aspect, the present invention provides the use of a compound of formula (I), or a pharmaceutically acceptable salt or solvate thereof, as hereinbefore defined in the manufacture of a medicament for use in therapy.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of chemokine receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CXCR2) receptor, which comprises administering to a patient a therapeutically effective amount of a compound of formula (I), or a pharmaceutically acceptable salt or solvate thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compounds of the invention are administered orally.

The invention will now be further illustrated by reference to the following examples. In the examples the Nuclear Magnetic Resonance (NMR) spectra were measured on a Varian Unity Inova 300 or 400 MHz spectrometer and the Mass Spectrometry (MS) spectra measured on a Finnigan Mat SSQ7000 or Micromass Platform spectrometer. Where necessary, the reactions were performed under an inert atmosphere of either nitrogen or argon. Chromatography was generally performed using Matrex Silica 60® (35–70 micron) or Prolabo Silica gel 60® (35–70 micron) suitable for flash silica gel chromatography. High pressure liquid chromatograply purification was performed using either a Waters Micromass LCZ with a Waters 600 pump controller, Waters 2487 detector and Gilson FC024 fraction collector or a Waters Delta Prep 4000. The abbreviations m.p. and DMSO used in the examples stand for melting point and dimethyl sulphoxide respectively.

EXAMPLE 1

2-[[(2,3-Difluorophenyl)methyl]thio]-5,7-dihydro-4-[[(1R)-2-hydroxy-1-methylethyl]amino]-6H-pyrrolo[2,3-d]pyrimidin-6-one (a) 4,6-Dihydroxy-2-mercapto-5-pyrimidineacetic acid, Ethyl Ester To a solution of sodium ethoxide [prepared from sodium metal (1.6 g) and ethanol] was added thiourea (5.28 g) and triethyl 1,1,2-ethane tricarboxylate (17 g). The mixture was heated under reflux for 8 hours. The solution was cooled to room temperature and the solid collected by filtration, washed with a little ether. The solid was dissolved in water (100 ml) and the pH adjusted to 6–7 by the addition of hydrochloric acid. No solid was precipitated therefore the solution was lyophilised to give a pink solid (8.1 g)

$^1$H NMR: δ (DMSO) 10.79 (2H, s), 3.97 (2H, q), 3.06 (2H, s), 1.14 (3H, t).

(b) 2-[[(2,3-Difluorophenyl)methyl]thio]-4,6-dihydroxy-5-pyrimidineacetic acid, Ethyl Ester To a suspension of 60% sodium hydride in oil (1.37 g) in dry DMF (10 ml) was added a solution of the product from example 1, step (a) (7.9 g) in dry DMF (30 ml). After the addition the mixture was stirred at room temperature for 1 hour. To the solution was added 2,3-difluorobenzylbromide (4.45 ml) and the mixture allowed to stir overnight. The mixture was poured into water (200 ml) and the product collected by filtration to give the subtitle compound (8.1 g).

MS: APCI 355 (M−H), 357 (M+H) $^1$H NMR: δ (DMSO) 7.50–7.18 (3H, m), 4.47 (2H, s), 4.04 (2H, q), 3.97 (2H, s), 1.67 (3H, t).

(c) 4,6-Dichloro-2-[[(2,3-difluorophenyl)methyl]thio]-5-pyrimidineacetic acid, Ethyl Ester A mixture of the product from example 1, step (b)(8.1 g) and phosphorus oxychloride (100 ml) was stirred at room temperature while N,N-dimethylaniline (2.91 ml) was added dropwise. The solution was then heated under reflux for 2 hours. The mixture was allowed to cool to room temperature and poured onto crushed ice/water. The crude product was extracted into ether. Chromatography on silica eluting with 10% methanol/isohexane afforded the subtitle compound (5.1 g).

MS: APCI 392 (M−H), 394 (M+H) $^1$H NMR: δ (DMSO) 7.32–6.98 (3H, m), 4.43 (2H, s), 4.23 (2H, q), 3.87 (2H, s), 1.28 (3H, t), (d) 4-Chloro-2-[[(2,3-difluorophenyl)methyl]thio]-6-[[(2,4-dimethoxyphenyl)methyl]amino]-5-pyrimidineacetic acid, Ethyl Ester To a solution of the product from example 1, step (c) (1.0 g) in dry DMF (30 ml) was added 2,4-dimethoxybenzylamine hydrochloride (0.52 g) followed by N,N'-diisopropylethylamine is (1 ml) and the mixture stirred at 40° C. for 1 hour. The mixture was evaporated to dryness. Chromatography on silica eluting with 10% ethyl acetate/dichloromethane afforded the subtitle compound (1.0 g).

MS: APCI 522 (M−H), 524 (M+H) $^1$H NMR: δ (DMSO) 7.28–7.22 (1H, m), 7.13–6.97 (3H, m), 6.45–6.42 (2H, m), 6.08 (1H, t), 4.57 (2H, s), 4.41 (2H, s), 4.16 (2H, q), 3.82 (3H, s), 3.79 (3H, s), 3.54 (2H, s), 1.22 (3H, t).

(e) 4-Chloro-2-[[(2,3-difluorophenyl)methyl]thio]-5,7-dihydro-6H-pyrrolo[2,3-d]pyrimidin-6-one, A solution of the product from example 1, step (d) (0.5 g) in dry toluene (50 ml) containing p-toluene sulphonic acid (25 mg) was heated under reflux for 4 hours. [Analysis of the reaction mixture by 1 c/ms indicated cyclisation was complete but with loss of the acid labile dimethoxybenzyl adduct.] The reaction mixture was evaporated to dryness and the residue purified by chromatography on silica eluting with ethyl acetate to afford the subtitle compound (0.20 g).

MS: APCI 328 (M+H)

(f) 2-[[(2,3-Difluorophenyl)methyl]thio]-5,7-dihydro4-[[(1R)-2-hydroxy-1-methylethyl]amino]-6H-pyrrolo[2,3-d]pyrimidin-6-one The product from example 1, step (e) (0.20 g) in NMP (5 ml) was treated with (R)-2-amino-1-propanol (0.56 g) and the reaction mixture was heated at 110° C. for 2 hours. The mixture was evaporated to dryness and the residue purified (HPLC, Symmetry® C18 column, 0.1% aqueous ammonium acetate:acetonitrile isocratic elution 75:25) to afford the title compound (0.055 g).

MS: APCI 367 (M+H) $^1$H NMR: δ (DMSO) 7.38–7.10 (3H, m), 6.74 (1H, d), 4.69 (1H, m), 4.38 (2H, s), 4.12 (1H, m), 3.43–3.29 (2H, m), 3.17 (2H, s), 1.08 (3H, d).

EXAMPLE 2

7,9-dihydro-6-[[(1R)-2-hydroxy-1-methylethyl]amino]-2-[(phenylmethyl)thio]-8H-purin-8-one a) 2-[(Phenylmethyl)thio]-4,6-pyrimidinediol To a solution of 4,6-dihydroxy-2-mercaptopyrimidine (100 g) in 5M NaOH (360 ml) was added first NMP (200 ml), then benzyl bromide (90 ml) dropwise over 2 hours. The reaction was stirred at room temperature for 24 hours, then acidified to pH 2 with conc HCl (100 ml) added dropwise over 2 hours at −5° C. to give a pink precipitate. This was isolated by decanting off the solution followed by trituration with diethyl ether (1 liter) to give the subtitled product as a white powder after filtration and drying (210 g).

m.p. 220–250° C. (dec) MS: APCI (−ve) 233 (M−H) $^1$H NMR: δ (DMSO) 11.76 (1H, br s), 7.45 (2H, d), 7.26 (3H, m), 5.18 (1H, s), 4.38 (2H, s).

b) 5-Nitro-2-[(phenylmethyl)thio]-4,6-pyrimidinediol

The product of example 2, step (a) (2 g) was added to a mixture of glacial acetic acid (50 ml) and concentrated nitric acid (20 ml) and the reaction mixture heated to 50° C. A further 28 g of the product of step (a) was added in portions over 2 hours whilst maintaining the reaction temperature between 50 and 60° C. After stirring the reaction mixture for a further 1 hour at 50° C. it was poured onto crushed ice and the subtitled product isolated by filtration as a yellow solid (12.3 g).

$^1$H NMR: δ (DMSO) 7.48–7.19 (5H, m), 4.47 (2H, s).

c) 4,6-Dichloro-5-nitro-2-[(phenylmethyl)thio]-pyrimidine

A suspension of the product of example 2, step (b) (59.2 g) in a mixture of POCl$_3$ (100 ml) and toluene (400 ml) was heated to 80° C. A solution of 1-methylimidazole (16.9 ml) in toluene (200 ml) was added dropwise over 1 hour and the reaction mixture then heated at 100° C. for 24 hours. After cooling to room temperature, the solvent was removed by evaporation and water (2 liters) cautiously added to the residue. The mixture was extracted with dichloromethane (4×500 ml) and the combined organic extracts dried over MgSO$_4$, filtered and evaporated to give a brown tar. This was purified by column chromatography, eluting with 10% dichloromethane in isohexane, to afford the subtitled product as a yellow solid (29.7 g).

MS: APCI (−ve) 315 (M−H) $^1$H NMR: δ (DMSO) 7.43–7.24 (5H, m), 4.40 (2H, s).

d) 6-chloro-5-nitro-2-[(phenylmethyl)thio]-4-pyrimidinamine

Ammonia solution (14 ml, 0.5 M in dioxane) was added dropwise to a solution of the product of example 2, step (c) (2.0 g) and diisopropylethylamine (3.31 ml) in THF (100 ml) over a 1 h period at RT. After stirring for a further 1 h the reaction was concentrated in vacuo onto silica and purified by column chromatography using 9:1 then 4:1 isohexane/ethyl acetate as eluent to yield the subtitled product as a yellow solid (980 mg, 52%).

MS: ESI (−ve) 296 (M−H, 100%)

e) 6-chloro-2-[(phenylmethyl)thio]-4,5-pyrimidinediamine

A suspension of the product from example 2, step (d) (980 mg), NH$_4$Cl (1.61 g) and iron powder (559 mg) in EtOH (100 ml) and H$_2$O (15 ml) was heated at 85° C. for 1.5 h. The mixture was filtered through celite and washed with hot MeOH (100 ml) before concentrating the filtrate onto silica under reduced pressure. Column chromatography using 1:1 isohexane/ethyl acetate as eluent provided the subtitled product as a yellow solid (0.69 g, 78%)

MS: ESI (−ve) 265 (M−H, 100%)

f) 6-chloro-7,9-dihydro-2-[(phenylmethyl)thio]-8H-purin-8-one

A solution of triphosgene (0.92 g) in DCM (25 ml) was added dropwise to a solution of the product from example 2, step (e) (0.69 g) and triethylamine (0.55 ml) in DCM (25 ml) at −10° C. The cooling bath was then removed and the suspension stirred for 2.5 h. Upon cooling to 0° C. NaHCO$_3$ (20 ml) was added with vigorous stirring before recovering the organics by extracting with DCM (3×50 ml). The organic extracts were combined, dried (MgSO$_4$) and concentrated in vacuo to yield a crude yellow solid. This material was triturated with EtOAc and filtered to afford a pink solid (360 mg, 48%). The filtrate was concentrated and again triturated with EtOAc to provide a second crop (170 mg, 70% overall)

MS: ESI (−ve) 291 (M−H, 100%)

g) 7,9-dihydro-6-[[(1R)-2-hydroxy-1-methylethyl]amino]-2-[(phenylmethyl)thio]-8H-purin-8-one A solution of the product from example 2, step (f) (0.1 g) in a mixture of alaninol (0.128 g), disopropylethylamine (0.35 ml) and N-methylpyrrolidinone (3 ml) was stirred at 100° C. for 48 h before pouring into H₂O (75 ml). 2M HCl solution was then added to pH=2 and the light brown solid formed filtered and recrystallised from EtOH to afford the subtitle compound (22 mg, 19%)

m.p. 284° C.

MS: ESI (−ve) 330 (M−H, 100%) ¹H NMR: δ (DMSO) 11.2 (1H, s), 9.82 (1H, s), 7.20–7.41 (5H, m), 6.40 (1H, d, J 10.8), 4.85 (2H, s), 4.30 (2H, s), 4.15 (1H, m), 3.43 (2H, m) and 1.14 (3H, d, J 7.4)

EXAMPLE 3

4-amino-2-[[(2,3-difluorophenyl)methyl]thio]-5,7-dihydro-6H-pyrrolo[2,3-d]pyrimidin-6-one, (a) 4-amino-5,7-dihydro-2-mercapto-6H-pyrrolo [2,3-d]pyrimidin-6-one, Prepared by the method of example 1, step (a), using 3,3-dicyano-propanoic Acid, Ethyl Ester.

MS: APCI 183 (M+H) ¹H NMR: δ (DMSO) 11.76 (1H, s), 10.97 (1H, s), 6.89 (2H, s), 3.23 (2H, s).

(b) 4-amino-2-[[(2,3-difluorophenyl)methyl]thio]-5,7-dihydro-6H-pyrrolo[2,3-d]pyrimidin-6-one, To a suspension of 60% sodium hydride (125 mg) in dry DMF (5 ml) was added a solution of the product from example 3, step (a) (0.57 g) in DMF (10 ml). The mixture was allowed to stir for 30 mins. To the solution was added 2,3-difluorobenzyl bromide (0.39 ml) and the mixture stirred for 2 hours. Poured into water and the crude product extracted into ethyl acetate. Chromatography on silica eluting with 10% ethyl acetate/dichloromethane afforded the title compound (0.35 g).

MS: APCI 309 (M+H) ¹H NMR: δ (DMSO) 10.85 (1H, s), 7.45–10 (3H, m), 6.78 (2H, m), 4.36 (2H, s), 3.24 (2H, s).

EXAMPLE 4

(2R)-2-[[8-amino-2-[[(2-fluorophenyl)methyl]thio]-9H-purin-6-yl]amino]-1-propanol, (a) 6-amino-2-[[(2-fluorophenyl)methyl]thio]-4-pyrimidinol, To a stirred suspension of 4-Amino-6-hydroxy-2-mercaptopyrimidine monohydrate (25 g) in DMF (300 ml) was added potassium hydroxide (10.2 g) and water (50 ml). After a clear solution was obtained, 2-fluorobenzyl bromide (29.3 g) was added and the reaction stirred at room temperature for 30 min. The mixture was poured into water (2l) and the resulting precipitate isolated by filtration, washing with isopropanol and diethyl ether, affording the subtitled compound as a white solid (34.7 g).

MS: APCI 252 (M+H) ¹H NMR: δ (DMSO) 11.42 (1H, br s), 7.61 (1H, t), 7.33 (1H, m), 7.16 (2H, m), 6.56 (2H, br s), 4.97 (1H, s), 4.35 (2H, s).

(b) 6-chloro-2-[[(2-fluorophenyl)methyl]thio]-4-pyrimidinamine

The product of example 4, step (a) (34 g) was added to a solution of 2-picoline (20 ml) in POCl₃ (150 ml) and the mixture refluxed for 24 hr. The reaction mixture was concentrated in vacuo to half its original volume and poured onto ice and then neutralized with ammonia, forming a brown gum. The aqueous phase was decanted off, and the organic residues dissolved in ethyl acetate. This solution was recombined with the aqueous phase, and refluxed for 1 hr. The organic phase was separated, evaporated, and the residue purified by silica gel chromatography, eluting with dichloromethane to afford the subtitled compound as a pale yellow solid (15.6 g).

MS: APCI (+ve) 270 (M+H, 100%) ¹H NMR: δ (DMSO) 7.57 (1H, t), 7.37 (2H, br s), 7.33 (1H, m), 7.14 (2H, m), 6.20 (1H, s), 4.32 (2H, s).

(c) (2R)-2-[[6-amino-2-[[(2-fluorophenyl)methyl]thio]4-pyrimidinyl]amino]-1-propanol A solution of the product from example 4, step (b) (15 g), triethylamine (15 ml) and D-alaninol (10 g) was heated at 160° C. for 18 h. The reaction mixture was allowed to cool to room temperature and poured into aqueous ammonium chloride (1l). The resultant white precipitate was purified by silica gel chromatography, eluting first with 1:1 DCM:ethyl acetate and then 3:1 DCM:methanol, giving the subtitled product as a yellow foam (10.7 g).

MS: APCI (+ve) 309 (M+H, 100%)

(d) (2R)-2[[6-amino-2-[[(2-fluorophenyl)methyl]thio]-5-nitroso4-pyrimidinyl]amino]-1-propanol To a stirred solution of the product from example 4, step (c) (10 g) in acetic acid (300 ml) at room temperature was added a solution of sodium nitrite (2.24 g) in water (30 ml). The reaction was stirred at 0° C. for 30 min, and the resultant purple precipitate isolated by filtration, washing with water, to give the subtitled compound as a dark blue solid (4.8 g).

MS: APCI (+ve) 338 (M+H, 100%)

(e) (2R)-2-[[5,6-diamino-2-[[(2-fluorophenyl)methyl]thio]-4-pyrimidinyl]amino]-1-propanol Sodium dithionite (4 g) was added in portions to a suspension of the product from example 4, step (d) (8.4 g) in a mixture of water (35 ml) and DMF (15 ml) at 100° C. The resultant yellow solution was cooled in an ice bath and 50% aqueous sulphuric acid (15 ml) was added, giving a grey precipitate. The mixture was stirred for 10 min, then filtered, washing with water, ethanol and diethyl ether, to afford the subtitled product as a grey solid (1.0 g).

MS: APCI (+ve) 324 (M+H, 100%)

(f) [2-[[(2-fluorophenyl)methyl]thio]-6-[[(1R)-2-hydroxy-1-methylethyl]amino]-9H-purin-8-yl]-carbamic acid, Ethyl Ester To a solution of ethoxycarbonylisothiocyanate (0.48 ml) in dry acetonitrile (20 ml) at 0° C. under an atmosphere of nitrogen was added a suspension of the product from example 4, step (e) (1.15 g) in dry acetonitrile (20 ml) containing 2.5 eq triethylamine. After stirring at 0° C. for 5 min, diisopropylcarbodiimide (0.8 ml) was added and the reaction warmed to 70° C. for 1 hr. The reaction mixture was concentrated in vacuo and the residue purified twice by silica gel chromatography, eluting both times with 3:1 ethyl acetate:DCM, to afford the subtitled product as a white solid (0.045 g).

MS: APCI (+ve) 421 (M+H, 100%) ¹H NMR: δ (DMSO) 11.87 (1H, br s), 11.41 (1H, br s), 7.56 (2H, m), 7.28 (1H, m), 7.14 (2H, m), 4.81 (1H, t), 4.36 (2H, s), 4.22 (3H, m), 3.46 (1H, m), 3.39 (1H, m), 1.28 (3H, t), 1.15 (3H, d).

(g) (2R)-2-[[8-amino-2-[[(2-fluorophenyl)methyl]thio]-9H-purin-6-yl]amino]-1-propanol A solution of the product from example 4, step (f) (0.042 g) and lithium hydroxide monohydrate (16 mg) in dioxan (4 ml) and water (2 ml) was heated under reflux for 5 hr. The reaction mixture was concentrated in vacuo and the residue purified by silica gel column chromatography, eluting with 4:1 DCM:ethanol containing 0.5% 880 ammonia, to afford the titled compound as a white solid (0.015 g).

m.p. 250–255° C. (dec) MS: APCI (+ve) 349 (M+H, 100%) ¹H NMR: δ (DMSO) 10.30 (1H, br s), 7.54 (1H, t), 7.28 (1H, m), 7.14 (2H, m), 6.64 (1H, br s), 6.47 (1H, br s), 4.77 (1H, br s), 4.34 (2H, s), 4.17 (1H, m), 3.45 (1H, m), 3.38 (1H, m), 1.13 (3H, d).

EXAMPLE 5

2-[[8-amino-2-[[(2,3-difluorophenyl)methyl]thio]-9H-purin-6-yl]amino]-1,3-propanediol a) 2-[[(2,3-Difluorophenyl)methyl]thio]-4,6-pyrimidinediamine 4,6-diamino-2-pyrimidinethiol (7.3 g) was dissolved in DMSO (100 ml) at room temperature under an atmosphere of nitrogen. Potassium tert-butoxide (1M in THF, 48.3 ml) was added followed by 2,3-difluorobenzyl-bromide (10.0 g). The mixture was stirred for 2 hours at room temperature. The reaction mixture was then partitioned between ethyl acetate and ammonium chloride. The organic phase was washed with ammonium chloride (3×) and brine, then dried over magnesium sulphate and evaporated to give the sub-titled product as a white solid (12.2 g)

MS: APCI (+ve) 269 (M+1)

b) 2-[[(2,3-Difluorophenyl)methyl]thio]-5-nitroso4,6-pyrimidinediamine

The product of example 5, step (a) (2.5 g) was dissolved in acetic acid (150 ml) and the solution cooled to 5° C. A solution of sodium nitrite (625 mg) in water (50 ml) was added dropwise resulting in a dark blue colouration. The reaction was stirred at room temperature for 30 minutes during which time a pink solid precipitated from solution. This was isolated by filtration and washed with water, then dried at 50° C. to give the sub-titled product as a blue solid (4.14 g)

MS: APCI (+ve) 298 (M+1) $^1$H NMR: δ (DMSO) 4.44 (s, 2H), 7.13–7.54 (in, 3H), 8.13 (s, 1H), 8.51 (s, 1H), 9.10 (s, 1H), 10.18 (s, 1H).

c) 2-[[(2,3-Difluorophenyl)methyl]thio]-4,5,6-pyrimidinetriamine

To a suspension of the product of example 5, step (b) (2 g) in boiling water (40 ml) was added $Na_2S_2O_4$ (5.4 g) portion-wise. The suspension was allowed to cool and then 50% sulphuric acid was added slowly and then the mixture was cooled to 0° C. The solid was isolated by filtration and washed with cold water, then dried over $P_2O_5$ at 50° C. to give the sub-titled product as a yellow solid.

MS: APCI (+ve) 284 (M+1) $^1$H NMR: δ (DMSO) 4.33 (s, 2H), 6.42 (br s, 3B), 7.10–7.48 (m, 3H)

d) Ethyl 6-amino-2-[(2,3-difluorobenzyl)thio]-9H-purin-8-ylcarbamate

A solution of the product of example 5, step (c) (10.5 g) in acetonitrile (50 ml) and triethylamine (17 ml) was added to an ice cold stirred solution of ethoxycarbonylisothiocy-anate (3 ml) in acetonitrile (50 ml). This mixture was then stirred at room temperature for 20 min. Diisopropylcarbo-diimide (4.5 ml) was then added and the reaction mixture was stirred at reflux for 2 hr and allowed to cool. The reaction mixture was evaporated to dryness and purified by flash chromatography on silica gel (ethyl acetate:dichloromethane, 1:1) to yield the sub-titled compound as a yellow solid (3.0 g).

MS: APCI (+ve) 381 (M+1)

e) Ethyl 6-bromo-2-[(2,3-difluorobenzyl)thio]-9H-purin-8-ylcarbamate

The product of example 5, step (d) (1 g) was dissolved in bromoform (14 ml) and iso-amyl nitrite (0.1 ml) and heated at 40° C. for 5 hr. The reaction mixture was then evaporated to dryness and purified by flash chromatography on silica gel with 20% ethyl acetate in dichloromethane, yielding the subtitled compound as a yellow solid (208 mg).

MS: APCI (+ve) 445 (M+1)

f) 2-[[8-amino-2-[[(2,3-difluorophenyl)methyl]thio]-9H-purin-6-yl]amino]-1,3-propanediol The product of example 5, step (e) (40 mg) was dissolved in NMP and 2-amino-1,3-propanediol (49.2 mg) and diiso-propylethylamine (31 μl) base was added and the solution was heated at 150° C. for 36 hr. The reaction mixture was then evaporated to a residue that was purified by preparative HPLC to yield the titled compound as a pale yellow solid (9.5 mg).

MS: APCI (+ve) 383 (M+1) $^1$H NMR: δ (DMSO) 3.52 (m, 4H), 4.17 (m, 1H), 4.41 (s, 2H), 4.78 (m, 2H), 7.13–7.45 (m, 3H), 7.59 (m, 1H).

EXAMPLE 6

2-[[8-amino-2-[[(2,3-difluorophenyl)methyl]thio]-9H-purin-6-yl]amino]-2-methyl-1-propanol The titled compound was prepared from the product of example 5, step (e) (50 mg) and 2-amino-2-methyl-1-propanol (66 μl) using the method of example 5, step (f) and purified by preparative HPLC to yield a white solid.

MS: APCI (+ve) 381 (M+1) $^1$H NMR: δ (DMSO) 0.98 (s, 6H), 3.13 (s, 2H), 3.49 (s, 1H), 4.39 (s, 2H), 6.48 (br s, 1H), 7.13–7.37 (m, 3H).

EXAMPLE 7

(2R)-2-[[8-amino-2-[[(2,3-difluorophenyl)methyl]thio]-9H-purin-6-yl]amino]-1-butanol The titled compound was prepared from the product of Example 5, step (e) (50 mg) and (2R)-2-amino-1-butanol (66 μl) using the method of example 5, step (f) and purified by preparative HPLC to yield a white solid.

MS: APCI (+ve) 381 (M+1) $^1$H NMR: δ (CDCl$_3$) 0.89 (m, 3H), 1.55–1.73 (m, 2H), 3.27 (m, 1H), 3.57 (m, 1H), 3.65 (m, 1H), 4.16 (m, 1H), 4.44 (s, 2H), 5.39 (br s, 2H), 5.73 (d, 1H), 6.97–7.34 (m, 3H).

EXAMPLE 8

2-[[8-amino-2-[[(2,3-difluorophenyl)methyl]thio]-9H-purin-6-yl]amino]-2-methyl-1,3-propanediol The titled compound was prepared from the product of example 5, step (e) (50 mg) and 2-amino-2-methyl-1,3-propanediol (70 mg) using the method of example 5, step (f) and purified by preparative HPLC to yield a white solid.

MS: APCI (+ve) 397 (M+1) $^1$H NMR: δ (DMSO) 7.37–7.11 (3H, m), 4.38 (2H, s), 3.63 (2H, d), 3.53 (2H, d), 1.25 (3H, s)

EXAMPLE 9

(2R)-2-[[8-amino-2-[[(2,3-difluorophenyl)methyl]thio]-9H-purin-6-yl]amino]-1-propanol a) 2,6-bis[[(2,3-difluorophenyl)methyl]thio]-4,5-pyrimidinediamine 5,6-diamino-2,4-pyrimidinedithiol (10.9 g, 62.6 mmol) was dissolved in a solution of KOH powder (85%) (7.72 g, 2.2eq) in methanol (250 ml). 2,3-difuorobenzyl bromide (22.5 g, 1.75eq) was added and the mixture was stirred at room temperature for 30 min. The resulting solution was poured in to 500 ml of water, whereupon a pale brown solid precipitated out which was collected by filtration and washed with 3× iso-propanol and 3× ether to give the subtitled product as a pale brown solid (15 g, 56%) which was dried in a vacuum oven.

MS: APCI (+ve) 427 (M+1)

b) 12,6-bis[[(2,3-difluorophenyl)methyl]thio]-9H-purin-8-yl]-, Ethyl Ester Carbamic Acid A solution of the product of example 9, step (a) (23 g) in hot acetonitrile (500 ml) was added to an ice-cold solution of ethoxycarbonyl isothiocyanate (7.6 ml, 1.2 eq) in aceto-nitrile (250 ml) and stirred at 0° C. for 30 min. Diisopro-pylcarbodiimide (12.6 ml, 1.5 eq) was then added and the reaction mixture was refluxed for 2 hr. The mixture was then cooled and the brown precipitate that formed was collected by filtration, washed with acetonitrile and ether and air dried to yield the sub-titled compound as a brown solid (20.5 g, 73%).

MS: APCI (+ve) 524 (M+1) $^1$H NMR: δ (DMSO) 1.26 (t, 3H), 4.22 (q, 2H), 4.49 (s,2H), 4.59 (s,2H), 7.12–7.48 (m,6H), 11.44 (bs,1H), 12.38 (bs,1H).

c) (2R)-2-[[8-amino-2-[[(2,3-difluorophenyl)methyl]thio]-9H-purin-6-yl]amino]-1-propanol The product of example 9, step (b) (5×1 g) was dissolved in hot D-alaninol (5×3 ml) in a sealed tube (5×10 ml capacity) and heated to 200° C. for 24 hr. The resulting solutions were combined and evaporated. The residue was purified first by flash chromatography on silica, eluting with ethyl acetate:methanol 10:1 (+0.5% 880 ammonia) followed by preparative HPLC to yield the titled product as a white solid (72 mg, 2%)

MS: APCI (+ve) 367 (M+1) ¹H NMR: δ (DMSO) 1.13 (d,3H), 3.41 (m,2H), 4.17 (m,1H), 4.37 (s,2H), 4.79 (bs,1H), 7.09–7.37 (m,3H).

EXAMPLE 10
2-[[8-amino-2-[[(2,3-difluorophenyl)methyl]thio]-9H-purin-6-yl]amino]-ethanol The titled compound was prepared from the product of example 9, step (b) (3 g) and ethanolamine (9 ml) using the method of example 9, step (c).

MS: APCI (+ve) 353 (M+1) ¹H NMR: δ (DMSO) 3.47 (s,2H), 3.55 (m,2H), 4.38 (s,2H), 4.79 (s,1H), 7.09–7.37 (m,3H),

EXAMPLE 11
(2R)-2-[[8-amino-2-[[(3-chlorophenyl)methyl]thio]-9H-purin-6-yl]amino]-1-propanol (a) 6-amino-2-[[(3-chlorophenyl)methyl]thio]-4-pyrimidinol, Prepared by the method of example 4, step (a) and 3-chlorobenzylbromide.

MS: APCI 267 (M+H)

(b) 6-chloro-2-[[(3-chlorophenyl)methyl]thio]-4-pyrimidinamine

Prepared by the method of example 4, step (b) using the product from example 11 step (a)

MS: APCI (+ve) 286 (M+H, 100%)

c) (2R)-2-[[6-amino-2-[[(3-chlorophenyl)methyl]thio]-4-pyrimidinyl]amino]-1-propanol Prepared by the method of example 4, step (c) using the product of example 11, step (b)

MS: APCI (+ve) 325 (M+H, 100%)

d) (2R)-2-[[6-amino-2-[[(3-chlorophenyl)methyl]thio]-5-nitroso-4-pyrimidinyl]amino]-1-propanol Prepared by the method of example 4, step (d) using the product of example 11, step (c).

MS: APCI (+ve) 354 (M+H, 100%)

(e) (2R)-2-[[5,6-diamino-2-[[(3-chlorophenyl)methyl]thio]-4-pyrimidinyl]amino]-1-propanol Prepared by the method of example 4, step (e) using the product from example 11, step (d).

MS: APCI (+ve) 340 (M+H, 100%)

(f) [2-[[(3-chlorophenyl)methyl]thio]-6-[[(1R)-2-hydroxy-1-methylethyl]amino]-1H-purin-8-yl]-carbamic acid, ethyl ester Prepared by the method of example 4, step (f) using the product of example 11, step (e) (7.01 g) to give the product as a peach coloured solid (2.20 g).

MS: APCI (+ve) 437 ¹H NMR: δ (DMSO) 11.87 (1H, s), 11.43 (1H, s), 7.55–7.57 (1H, d), 7.49 (1H, s), 7.38–7.40 (1H,d), 7.33 (2H,m), 4.79–4.83 (1H,t), 4.33 (2H, s), 4.19–4.26 (1H+2H, m), 3.37–3.49 (2H, m), 1.25–1.29 (3H, t), 1.14–1.17 (3H, d).

g) (2R)-2-[[8-amino-2-[[(3-chlorophenyl)methyl]thio]-1H-purin-6-yl]amino]-1-propanol Prepared by the method of example 4, step (g) using the product of example 11, step (f) (0.25 g) to give the product as a colourless solid (0.096 g).

MS: APCI (+ve) 365 ¹H NMR: δ (DMSO) 7.47 (1H, s), 7.24–7.39 (3H, m), 6.65 (1H, br s), 6.51 (1H, br s), 4.77 (1H, br s), 4.26–4.36 (2H, t), 4.15 (1H, br s), 3.35–3.49 (2H, m), 1.11–1.13 (3H, d).

EXAMPLES 12–20

Examples 12 to 20 were prepared by first adding a solution of the appropriate benzyl halide (5×10⁻⁶ mol) in THF to a solution of (2R)-2-[(8-amino-2-mercapto-1H-purin-6-yl)amino]-1-propanol (5×10⁻⁶ mol) and sodium borohydride (large excess) in DMSO (0.1 ml) and ethanol (0.1 ml). The reaction mixture was allowed to stand overnight at room temperature.

The solvents were removed by evaporation and the resulting residue was taken up in dioxan (0.2 ml) and water (0.1 ml). To this a solution of lithium hydroxide monohydrate (4×10⁻⁵ mol) in water (0.04 ml) was added and the reaction mixture heated at 60° C. for 22 hours. The mixture was neutralised with HCl, solvents removed by evaporation, and the residue was made up to a concentration of 10 mmol using DMSO (0.5 ml).

(2R)-2-[(8-amino-2-mercapto-1H-purin-6-yl)amino]-1-propanol

To a solution of the product from example 11, step (f) (760 mg) in liquid ammonia was added sodium metal until a consistent blue colour persisted. To this mixture was added powdered ammonium chloride until the blue colour had been quenched. The ammonia was allowed to evaporate and the residual solid was then dissolved in water (50 ml), filtered, then the pH adjusted to 6–7 by the addition of hydrochloric acid. The precipitated solid was then collected by filtration and dried in vacuo to give the subtitle compound (220 mg).

MS: APCI (+ve) 313 (M+H, 100%)

EXAMPLE 12
(2R)-2-[[8-amino-2-[(phenylmethyl)thio]-9H-purin-6-yl]amino]-1-propanol MS: APCI (+ve) 331 (M+1).

EXAMPLE 13
(2R)-2-[[8-amino-2-[[(3-methylphenyl)methyl]thio]-9H-purin-6-yl]amino]-1-propanol MS: APCI (+ve) 345 (M+1)

EXAMPLE 14
(2R)-2-[[8-amino-2-[[(2-methylphenyl)methyl]thio]-9H-purin-6-yl]amino]-1-propanol MS: APCI (+ve) 345 (M+1)

EXAMPLE 15
(2R)-2-[[8-amino-2-[[(3-methoxyphenyl)methyl]thio]-9H-purin-6-yl]amino]-1-propanol MS: APCI (+ve) 361 (M+1)

EXAMPLE 16
(2R)-2-[[8-amino-2-[[(4-methylphenyl)methyl]thio]-9H-purin-6-yl]amino]-1-propanol MS: APCI (+ve) 345 (M+1)

EXAMPLE 17
(2R)-2-[[8-amino-2-[[(2-bromophenyl)methyl]thio]-9H-purin-6-yl]amino]-1-propanol MS: APCI (+ve) 411 (M+1)

EXAMPLE 18
(2R)-2-[[8-amino-2-[[(3-chloro-2-fluorophenyl)methyl]thio]-9H-purin-6-yl]amino]-1-propanol MS: APCI (+ve) 383 (M+1)

EXAMPLE 19
(2R)-2-[[8-amino-2-[[(3-chloro-4-methoxyphenyl)methyl]thio]-9H-purin-6-yl]amino]-1-propanol MS: APCI (+ve) 395 (M+1)

EXAMPLE 20
(2R)-2-[[8-amino-2-[(1,3-benzodioxol-4-ylmethyl)thio]-9H-purin-6-yl]amino]-1-propanol MS: APCI (+ve) 375 (M+1)

Pharmacological Data
Ligand Binding Assay

[$^{125}$I]IL-8 (human, recombinant) was purchased from Amersham, U.K. with a specific activity of 2,000 Ci/mmol. All other chemicals were of analytical grade. High levels of hrCXCR2 were expressed in HEK 293 cells (human embryo kidney 293 cells ECACC No. 85120602) (Lee et al. (1992) *J. Biol. Chem.* 267 pp 16283–16291). hrCXCR2 cDNA was amplified and cloned from human neutrophil mRNA. The DNA was cloned into PCRScript (Stratagene) and clones were identified using DNA. The coding sequence was subcloned into the eukaryotic expression vector RcCMV (Invitrogen). Plasmid DNA was prepared using Quiagen Megaprep 2500 and transfected into HEK 293 cells using Lipofectamine reagent (Gibco BRL). Cells of the highest expressing clone were harvested in phosphate-buffered saline containing 0.2% (w/v) ethylenediaminetetraacetic acid (EDTA) and centrifuged (200 g, 5 min.). The cell pellet was resuspended in ice cold homogenisation buffer [10 mM HEPES (pH 7.4), 1 mM dithiothreitol, 1 mM EDTA and a panel of protease inhibitors (1 mM phenyl methyl sulphonyl fluoride, 2 μg/ml soybean trypsin inhibitor, 3 mM benzamidine, 0.5 μg/ml leupeptin and 100 μg/ml bacitracin)] and the cells left to swell for 10 minutes. The cell preparation was disrupted using a hand held glass mortar/PTFE pestle homogeniser and cell membranes harvested by centrifugation (45 minutes, 100,000 g, 4° C.). The membrane preparation was stored at −70° C. in homogenisation buffer supplemented with Tyrode's salt solution (137 mM NaCl, 2.7 mM KCl, 0.4 mM NaH$_2$PO$_4$), 0.1% (w/v) gelatin and 10% (v/v) glycerol.

All assays were performed in a 96-well MultiScreen 0.45 μm filtration plates (Millipore, U.K.). Each assay contained ~50 pM [$^{125}$I]IL-8 and membranes (equivalent to ~200,000 cells) in assay buffer [Tyrode's salt solution supplemented with 10 mM HEPES (pH 7.4), 1.8 mM CaCl$_2$, 1 mM MgCl$_2$, 0.125 mg/ml bacitracin and 0.1% (w/v) gelatin]. In addition, a compound of formula (I) according to the Examples was pre-dissolved in DMSO and added to reach a final concentration of 1% (v/v) DMSO. The assay was initiated with the addition of membranes and after 1.5 hours at room temperature the membranes were harvested by filtration using a Millipore MultiScreen vacuum manifold and washed twice with assay buffer (without bacitracin). The backing plate was removed from the MultiScreen plate assembly, the filters dried at room temperature, punched out and then counted on a Cobra γ-counter.

The compound of formula (I) according to the Examples was found to have IC$_{50}$ values of less than (<) 10 μM.

Intracellular Calcium Mobilisation Assay

Human neutrophils were prepared from EDTA-treated peripheral blood, as previously described (Baly et al. (1997) Methods in Enzymology 287 pp 70–72), in storage buffer [Tyrode's salt solution (137 mM NaCl, 2.7 mM KCl, 0.4 mM NaH$_2$PO$_4$) supplemented with 5.7 mM glucose and 10 mM HEPES (pH 7.4)].

The chemokine GROα (human, recombinant) was purchased from R&D Systems (Abingdon, U.K.). All other chemicals were of analytical grade. Changes in intracellular free calcium were measured fluorometrically by loading neutrophils with the calcium sensitive fluorescent dye, fluo-3, as described previously (Merritt et al. (1990) Biochem. J. 269, pp513–519). Cells were loaded for 1 hour at 37° C. in loading buffer (storage buffer with 0.1% (w/v) gelatin) containing 5 μM fluo-3 AM ester, washed with loading buffer and then resuspended in Tyrode's salt solution supplemented with 5.7 mM glucose, 0. 1% (w/v) bovine serum albumin (BSA), 1.8 mM CaCl$_2$ and 1 mM MgCl$_2$. The cells were pipetted into black walled, clear bottom, 96 well micro plates (Costar, Boston, U.S.A.) and centrifuged (200 g, 5 minutes, room temperature).

A compound of formula (I) according to the Examples was pre-dissolved in DMSO and added to a final concentration of 0.1% (v/v) DMSO. Assays were initiated by the addition of an A$_{50}$ concentration of GROα and the transient increase in fluo-3 fluorescence ($\lambda_{Ex}$=490 nm and $\lambda_{Em}$=520 nm) monitored using a FLIPR (Fluorometric Imaging Plate Reader, Molecular Devices, Sunnyvale, U.S.A.).

The compounds of formula (I) according to the Examples were tested and found to be antagonists of the CXCR2 receptor in human neutrophils.

What is claimed is:

1. A compound of formula (I) and pharmaceutically acceptable salts or solvates thereof:

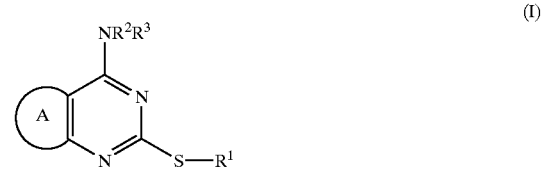

in which:

A is a group of formula (a) or (b):

R$^1$ represents a C$_3$–C$_7$ carbocydic, C$_1$–C$_8$ alkyl, C$_2$–C$_6$ alkenyl or C$_2$–C$_6$ alkynyl group, the latter four groups may be optionally substituted by one or more substituent groups independently selected from halogen atoms, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^{10}$, an aryl or heteroaryl group either of which can be optionally substituted by one or more substituents independently selected from halogen atoms, cyano, nitro, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^5$SO$_2$R$^{10}$, C$_1$–C$_6$ alkyl or trifluor R$^2$ and R$^3$ each independently represent hydrogen, a C$_3$–C$_7$ carbocyclic group, C$_1$–C$_8$ alkyl, C$_2$–C$_6$ alkenyl or C$_2$–C$_6$ alkynyl group, the latter four groups may be optionally substituted by one or more substituent groups independently selected from halogen atoms , —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^{10}$ or a 3–8 membered ring optionally containing one or more atoms selected from O, S, NR$^8$ and itself optionally substituted by C$_{1-3}$-alkyl, halogen, R$^4$ represents hydrogen, C$_1$–C$_6$ alkyl or a phenyl group the latter two of which maybe optionally substituted by one or more substituent groups independently selected from halogen atoms, phenyl, —OR$^{11}$ and —NR$^{12}$R$^{13}$;

R$^5$ and R$^6$ independently represent a hydrogen atom or a C$_1$–C$_6$ alkyl or phenyl group the latter two of which may be optionally substituted by one or more substituent groups independently selected from halogen atoms, phenyl, —OR$^{14}$ and —NR$^{15}$R$^{16}$, —CONR$^{15}$R$^{16}$, —NR$^{15}$COR$^6$, —SO$_2$NR$^{15}$R$^{16}$, NR$^{15}$SO$_2$R$^6$ or R$^5$ and R$^6$ together with the nitrogen atom to which they are attached form a 4- to 7-membered saturated heterocyclic ring system optionally comprising a further heteroatom selected from oxygen and nitrogen atoms, which ring system may be optionally substituted by one or more substituent groups independently selected from phenyl, —OR$^{14}$, —COOR$^{14}$, NR$^{15}$R$^{16}$ —CONR$^{15}$R$^{16}$, —NR$^{15}$COR$^{16}$, —SO$_2$NR$^{15}$R$^{16}$, NR$^{15}$SO$_2$R$^{16}$ or C$_1$–C$^6$ alkyl itself optionally substituted by one or more substituents independently selected from halogen atoms and —NR$^{15}$R$^{16}$ and —OR$^{17}$ groups;

R$^{10}$ represents a C$_1$–C$^6$ alkyl group or phenyl group, each of which may be optionally substituted by one or more substituent groups independently selected from halogen atoms, phenyl, —OR$^7$ and —NR$^{15}$R$^{16}$;

X is NH;

Y is N ; and each of R$^7$, R$^8$, R$^9$, R$^{11}$, R$^{12}$, R$^{13}$, R$^{14}$R$^{15}$, R$^{16}$, and R$^{17}$, -independently represent a hydrogen atom, C$_1$–C$_6$, alkyl, or a phenyl group.

2. The compound according to claim 1, wherein A is a group of formula (b) and Y is N.

3. The compound according to claim 1, wherein R$^1$ represents an optionally substituted benzyl group.

4. The compound according to claim 1, wherein one of R$^2$ and R$^3$ is hydrogen and the other is C$_3$–C$_8$ alkyl substituted by one or more hydroxy groups.

5. A compound selected from the group consisting of:
7,9-dihydro-6-[[(1R)-2-hydroxy-1-methylethyl]amino]-2-[(phenylmethyl)thio]-8H-purin-8-one,
(2R)-2-[[8-amino-2-[[(2-fluorophenyl)methyl]thiol-]9H-purin-6-yl]amino]-1-propanol,
2-[[8-amino-2-[[(2,3-difluorophenyl)methyl]thio]-9H-purin-6-yl]amino]-1,3-propanediol,
2-[[8-amino-2-[[(2,3-difluorophenyl)methyl]thio]-9H-purin-6-yl]amino]-2methyl-1-propanol,
2-[[8-amino-2-[[(2,3-difluorophenyl)methyl]thio]-9H-purin-6-yl]amino]-1-butanol,
2-[[8-amino-2-[[(2,3-difluorophenymethyl]thio]9H-purin-6yl]amino]-2-methyl-1,3-propanediol,
(2R)-2-[[8-amino-2-[[(2,3-difluorophenyl)methyl]thio]-9H-purin-6-yl]amino]-1-propanol,
2-[[8-amino-2-[[(2,3-difluorophenyl)methyl]thiol-9H-purin-6-yl]amino]-ethanol
(2R)-2-[[8-amino-2-[[(3-chlorophenyl)methyl]thiol-9H-purin-6-yl]amino]-1-propanol,
(2R)-2-[[8-amino-2-[(phenylmethyl)thio]9H-purin-6-yl]amino]-1-propanol,
(2R)-2-[[8-amino-2-[[(3-methylphenyl)methyl]thio]-9H-purin-6-yl]amino]-1-propanol,
(2R)-2-[[8-amino-2-[[(2-methylphenyl)methyl]thio]-9H-purin-6-yl]amino]-1-propanol,
(2R)-2-[[8-amino-2-[[(3-methoxypheny)methyl]thio]-9H-purin-6-yl]amino]-1-propanol,
(2R)-2-[[8-amino-2-[[(4-methylphenyl)methyl]thio]-9H-purin-6-yl]amino]-1-propanol,
(2R)-2-[[8-amino-2-[[(2-bromophenyl)methyl]thio]-9H-purin-6-yl]amino]-1-propanol,
(2R)-2-[[8-amino-2-[[(3-chloro-2-fluorophenyl)methyl]thio]-9H-purin-6-yl]amino]-1-propanol,
(2R)-2-[[8-amino-2-[[(3-chloro-4-methoxyphenyl)methyl]thio]-9H-purin]-6-yl]amino]-1-propanol, and
(2R)-2-[[8-amino-2-](1,3-benzodioxol-4-ylmethyl)thio]-9H-purin-6-yl]amino]1-propanol, and their pharmaceutically acceptable salts and solvates.

6. A process for the preparation of a compound of formula (1) as defined in claim 1 which comprises:

(a) treatment of a compound of formula (VI):

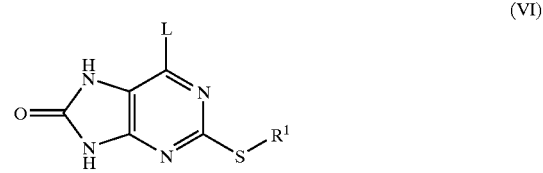

(VI)

where R$^1$ is as defined in formula (I) and L is a leaving group with an amine HNR$^2$R$^3$ or (b) treatment of a compound of formula (XII):

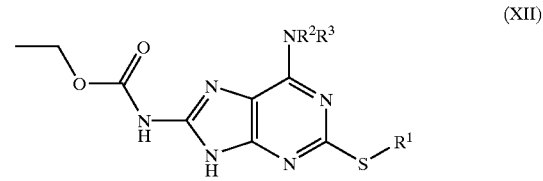

(XII)

where R$^1$, R$^2$ and R$^3$ are as defined in formula (I) with a hydrolysing agent, or (c) treatment of a compound of formula (XVIII):

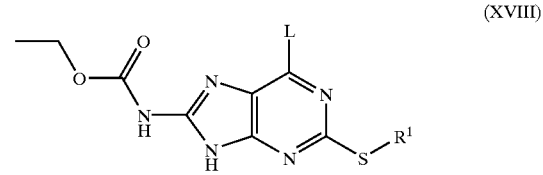

(XVIII)

where R$^1$ is as defined in formula (I) and L is a leaving group with an amine HNR$^2$R$^3$, or (d) treatment of a compound of formula (XXIII):

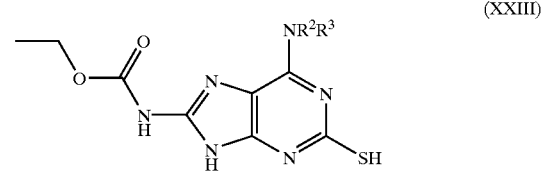

(XXIII)

where R² and R³ are as defined in formula (I) with an alkyl halide R¹X, or (e) treatment of a compound of formula (XXIV):

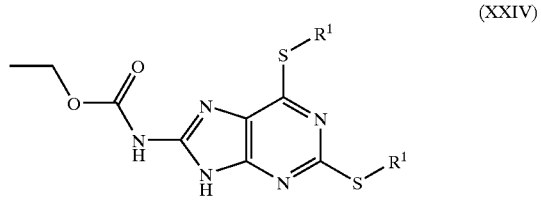
(XXIV)

where R¹ is as defined in formula (I) with an amine HNR2R3, and optionally thereafter (a), (b), (c), (d), or (e) forming a pharmaceutically acceptable salt.

7. A pharmaceutical composition comprising a compound of formula (I), or a pharmaceutically acceptable salt or solvate thereof, as claimed in claim 1 in association with a pharmaceutically acceptable adjuvant, diluent or carrier.

8. A process for the preparation of a pharmaceutical composition as claimed in claim 7 which comprises mixing the compound of formula (I), or a pharmaceutically acceptable salt or solvate thereof, with a pharmaceutically acceptable adjuvant, diluent or carrier.

* * * * *